(12) United States Patent
Gross

(10) Patent No.: US 11,083,612 B2
(45) Date of Patent: Aug. 10, 2021

(54) TRANS-AORTIC PROXIMAL AORTIC STENT GRAFT

(71) Applicant: Christian-Albrechts-Universitaet zu Kiel, Kiel (DE)

(72) Inventor: Justus Gross, Laboe (DE)

(73) Assignee: Universitaet Rostock, Rostock (DE)

( * ) Notice: Subject to any disclaimer, the term of this patent is extended or adjusted under 35 U.S.C. 154(b) by 29 days.

(21) Appl. No.: 16/071,761

(22) PCT Filed: Jan. 20, 2017

(86) PCT No.: PCT/DE2017/100031
§ 371 (c)(1),
(2) Date: Jul. 20, 2018

(87) PCT Pub. No.: WO2017/129168
PCT Pub. Date: Aug. 3, 2017

(65) Prior Publication Data
US 2019/0029855 A1     Jan. 31, 2019

(30) Foreign Application Priority Data
Jan. 25, 2016   (DE) ..................... 10 2016 101 272.6

(51) Int. Cl.
*A61F 2/966*      (2013.01)
*A61F 2/07*       (2013.01)

(52) U.S. Cl.
CPC .............. *A61F 2/9662* (2020.05); *A61F 2/07* (2013.01); *A61F 2002/9665* (2013.01)

(58) Field of Classification Search
CPC .. A61F 2/95; A61F 2/954; A61F 2/962; A61F 2/966; A61F 2002/9511;
(Continued)

(56) References Cited

U.S. PATENT DOCUMENTS

| 5,242,452 A | 9/1993 | Inoue |
| 2003/0065385 A1 | 4/2003 | Weadock |

(Continued)

FOREIGN PATENT DOCUMENTS

| DE | 602005005567 T2 | 4/2009 |
| DE | 102012101103 B3 | 7/2013 |

(Continued)

OTHER PUBLICATIONS

International Search Report dated Apr. 4, 2017, in International Application No. PCT/DE2017/100031.

*Primary Examiner* — Melanie R Tyson
(74) *Attorney, Agent, or Firm* — Stephan A. Pendorf; Patent Central LLC

(57) ABSTRACT

A trans-aortic proximal aortic stent graft [TAPAS graft] for introducing into a blood vessel. A a tubular sheath which encases a folded self-expanding stent from the inside as well as from the outside such that a sheath outer wall of the sheath lies against the self-expanding stent from the outside and a sheath inner wall lies against the self-expanding stent from the inside and keeps the self-expanding stent folded. The self-expanding stent is surrounded by the sheath at the distal end in the transition from the sheath inner wall to the sheath outer wall, and the self-expanding stent is provided with an anchor at the proximal end. Also, a method for using a trans-aortic proximal aortic stent graft [TAPAS graft].

4 Claims, 2 Drawing Sheets

(58) Field of Classification Search
CPC ...... A61F 2002/9505; A61F 2002/9528; A61F 2002/9534; A61F 2002/9665
See application file for complete search history.

(56) References Cited

U.S. PATENT DOCUMENTS

| | | |
|---|---|---|
| 2006/0025844 A1 | 2/2006 | Majercak et al. |
| 2007/0233220 A1* | 10/2007 | Greenan ............... A61F 2/07 623/1.11 |
| 2010/0016940 A1 | 1/2010 | Shokoohi et al. |
| 2011/0257720 A1* | 10/2011 | Peterson ............... A61F 2/243 623/1.11 |
| 2013/0204351 A1 | 8/2013 | Cox et al. |
| 2014/0200649 A1* | 7/2014 | Essinger ............... A61F 2/2439 623/1.12 |
| 2014/0336745 A1 | 11/2014 | Barthold et al. |

FOREIGN PATENT DOCUMENTS

| | | |
|---|---|---|
| EP | 2727563 A1 | 5/2014 |
| WO | 03079935 A1 | 10/2003 |
| WO | 2006037086 A1 | 4/2006 |
| WO | 2008066923 A1 | 6/2008 |
| WO | 2014108895 A2 | 7/2014 |
| WO | 2015075708 A1 | 5/2015 |

\* cited by examiner

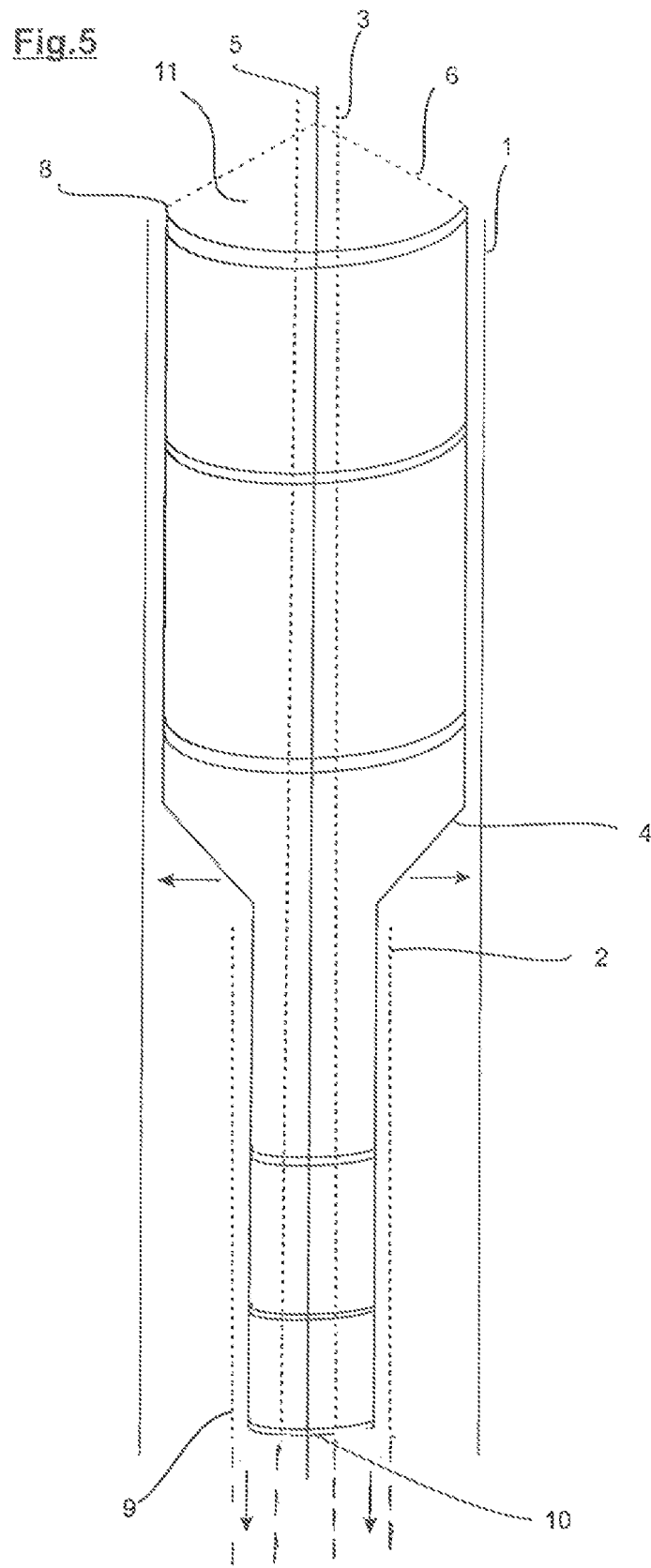

TRANS-AORTIC PROXIMAL AORTIC STENT GRAFT

BACKGROUND OF THE INVENTION

Field of the Invention

The invention relates to a Trans Aortic Proximal Aortic Stent-Graft [TAPAS-Graft] for insertion into a blood vessel, with a tube-like sheath that envelops a folded, self-expanding prosthesis both from the inside and the outside such that a sheath outer wall of the sheath lies against the prosthesis from the outside and a sheath inner wall lies against the prosthesis from the inside and keeps the prosthesis folded, in which the prosthesis is surrounded by the sheath at the distal end in the transition from the sheath inner wall to the sheath outer wall, and the prosthesis is provided with an anchor at the proximal end.

The invention further relates to a method for using a Trans Aortic Proximal Aortic Stent-Graft [TAPAS graft].

Description of the Related Art

From the state of the art, for example from the document DE 10 2012 101 103 B3, a stent graft with fixation elements and an insertion system is known. In this case, the stent graft has sections with a self-expanding stent which, in their longitudinal direction, have successively arranged rings of meander-shaped supports with a prosthesis material attached to rings. These rings each have fixing areas on loop-shaped fixing elements.

Furthermore, the document DE 60 2005 005 567 T2 shows an insertion device with a low unfolding force, which allows a step-wise unfolding of defined stent sections.

It is an object of the present invention to provide a Trans Aortic Proximal Aortic Stent Graft (TAPAS Graft) that is minimally invasively introduceable in a controlled manner into a blood vessel and employs a folded prosthesis and is unfolded from the proximal end to the distal end of the prosthesis.

A further object is to accurately position and deploy in a body a prosthesis of the inventive Trans Aortic Proximal Aortic Stent Graft (TAPAS-graft).

A further object is to separate the inserted prosthesis of the Trans Aortic Proximal Aortic Stent-Graft (TAPAS-Graft), after insertion via a guide, from this guide by a mechanism of the prosthesis and to pull out the guide, together with the sheath, from the blood vessel.

BRIEF SUMMARY OF THE INVENTION

These objects are achieved by the inventive Trans Aortic Proximal Aortic Stent-Graft and the method of using a Trans Aortic Proximal Aortic Stent-Graft (TAPAS Graft) of the independent claims.

The Trans Aortic Proximal Aortic Stent-Graft [TAPAS Graft] for introduction into a blood vessel is formed with a tube-like sheath that envelops a folded, self-expanding prosthesis both from the inside and the outside such that a sheath outer wall of the sheath lies against the prosthesis from the outside and a sheath inner wall lies against the prosthesis from the inside and keeps the prosthesis folded, in which the prosthesis is surrounded by the sheath at the distal end in the transition from the sheath inner wall to the sheath outer wall, and the prosthesis is provided with an anchor at the proximal end.

Further, a guide may be introduced in the sheath, particularly a guide catheter, which is releasably connected with the anchoring to the prosthesis via a releasable fixation with a release mechanism.

The releasable connection can be implemented with a cord-splint mechanism as release mechanism.

The method for use of the disclosed and described herein Trans Aortic Proximal Aortic Stent-Graft [TAPAS Graft], includes the steps of:
fixing the TAPAS graft to a guide, wherein the releasable fixation with the trigger mechanism connects the guide to the anchor on the prosthesis,
introducing the TAPAS graft via the guide (into a blood vessel), preferably under image converter (BV) control,
Releasing the TAPAS graft by fully releasing and deploying the folded, self-expanding prosthesis by pulling out the sheath and thereby engaging the prosthesis on a blood vessel wall;
positioning the prosthesis via the guide fixed with the anchoring to the prosthesis and releasably fixing with release mechanism to the anchor,
separating the prosthesis from the guide by actuation of the release mechanism,
removing the guide with the sheath.

The innovative stent-graft prosthesis is suitable with an antegrade operative process for the treatment of:
a) B-dissection
b) intramural hematomas of the descending aorta
c) penetrating aortic ulcer
d) aneurysm (verum or dissekans of the descending aorta)
(a-d) in pronounced calcification or occlusion of the abdominal aorta, the pelvis and afford arteries
e) A-dissection
after ascending or (partial) arch replacement, the stent treatment is transprothesial of residual dissection in the proximal descending aorta
a foregoing of the use of an "elephant trunk" or "frozen elephant trunk".

About the functionality of the TAPAS graft:
The surgical approach can take place
a) transaortal via the aortic arch
b) via the left subclavian artery
c) via an introduced ascending prothesis.

Structurally the TAPAS-graft is based on the possibility of introducing the stent graft prosthesis antegrade using BV-control and to be able to release from proximal to distal. This way an exact placement of the proximal portion is guaranteed.

The stent graft is "packed" between the sheath inner wall and the sheath outer wall and guided via a rigid guide catheter, for example Back up Meyer or Lundaquist under BV control in the aortic lumen. The prosthesis is coupled via a previously disclosed placement mechanism and a holding mechanism via a cord-splint mechanism to the proximal carrier system.

The sheath of TAPAS grafts has a shortened external and a continuous inner wall, wherein the two layers are bonded together at the distal end. By manually advancing the sheath, the stent graft unfolds successively as the end of the outer sheath wall slides past the "packed" stent graft.

After complete unfolding of the stent graft the prosthesis can be positioned via the cord-splint mechanism. The removal of the entire sheath then takes place retrograde through the lumen of the endostent graft.

The construction of the Trans Aortic Proximal Aortic Stent-Graft (TAPAS graft) provides a compact stent-graft system with a tubular, folded prosthesis that can be delivered through a guide, such as a guiding catheter, which is providable releasably fixable on the prosthesis via a release mechanism.

BRIEF DESCRIPTION OF THE SEVERAL VIEWS OF THE DRAWINGS

In the following, embodiments of the invention will be described in detail with reference to the accompanying drawings in the description of the figures, which are intended to illustrate the invention and are not to be considered as limiting.

There is shown in.

DETAILED DESCRIPTION OF THE INVENTION

Figure 1:
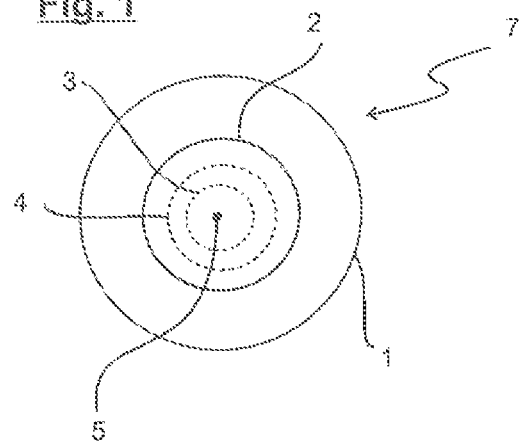
FIG. 1 an inventive device in a first position in cross section.

In FIG. 1 an inventive TAPAS graft 7 is shown in a first position ins cross-section. From outside to inside, the figure shows a blood vessel wall 1 and a tube-like, folded prosthesis 4 held between a sheath outer wall 2, and sheath inner wall 3.

Figure 2:
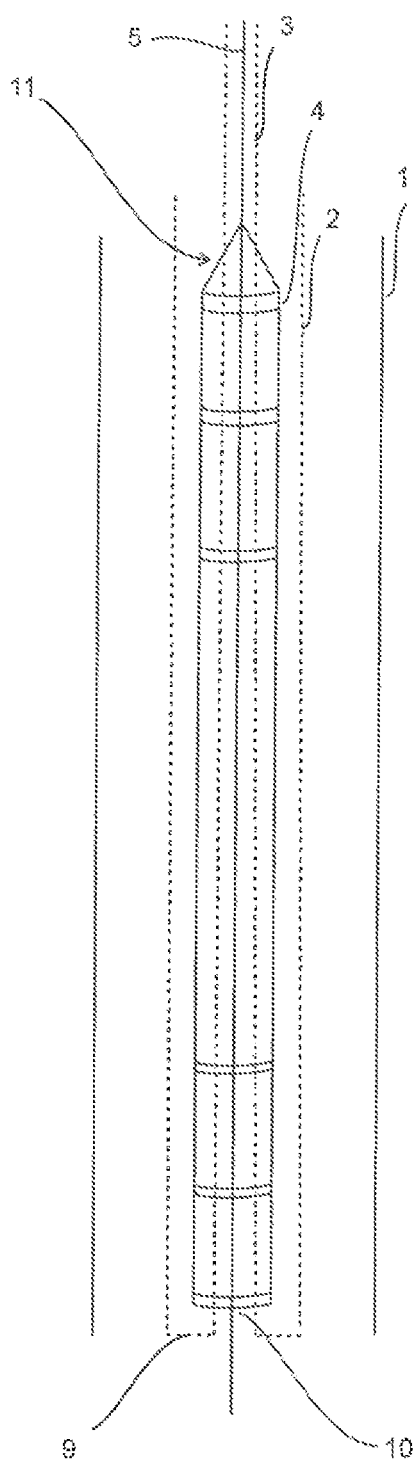
FIG. 2 an inventive device in the first position shown in FIG. 3 in longitudinal section.
Figure 3:
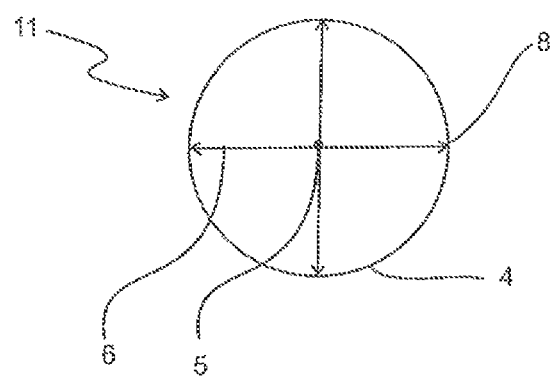
FIG. 3 a proximal anchor on a prosthesis in the first position in cross section.
Figure 4:
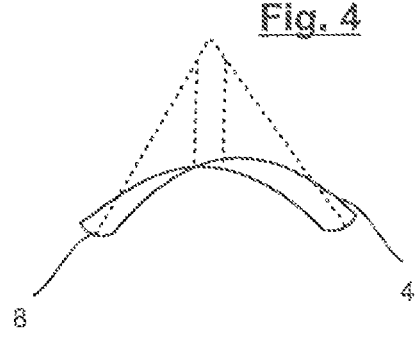
FIG. 4 a proximal anchor of the release mechanism in the first position in perspective lateral view and FIG. 5 in an inventive device in the second position in longitudinal section.

FIG. 2 shows an inventive TAPAS graft 7 in a first position in longitudinal section. From outside to inside, the figure shows a blood vessel wall 1 and a prosthesis 4 held between a sheath outer wall 2 and sheath inner wall 3. The inventive TAPAS graft 7 is releasably fixed to the prosthesis 4 to a centrally located guide 5, in particular a guide catheter or guide wire, via an anchor 8, The anchor 8 on the prosthesis 4 is releasably connected to the proximal end of the guide 5, which in the figure is at the top, with a release mechanism 6, wherein this preferably works by a cord-splint mechanism such that after an unfolding of the prosthesis 4 with the pulling out of the sheath and the guide the connection of the prosthesis 4 with the guide 5 can be released with the release by the release mechanism 6, FIG. 3 shows an anchor 8 with releasable fixation 6 on the guide 5 of the trigger mechanism in the first position in cross section at the proximal end 11 of the prosthesis 4. Here, for example, a cord-splint mechanism can be effective, FIG. 4 shows an anchor with releasable fixation 6 of the release mechanism in the first position in the cross section at the proximal end 11 of the prosthesis 4.

FIG. 5 shows an inventive TAPAS graft 7 in a second position in longitudinal section. This second position shows a partial unfolding of the prosthesis 4, by a partial removal or displacement of the sheath outer wall 2, wherein individual elements sections of the prosthesis 4 in the upper region of the figure ding to the blood vessel wall 1. The sheath 9 is moved by pulling on the guide 5 and thus frees the unfolding process of the prosthesis 4.

In the lower part of the figure, i.e. at the distal end 10, the prosthesis 4 is still held between the outer sheath wall 2 and sheath inner wall 3.

The inventive TAPAS graft 4 is releasably fixed to a centrally located guide 5. The detachable fixation 6 takes place on the (in the figure top) shown proximal end of the prosthesis 4 and preferably only after the complete deployment of the prosthesis 4 is it released from this and pulled out with the guide 5.

LIST OF REFERENCE NUMBERS

1 Blood vessel wall
2 Sheath outer wall
3 Sheath inner wall
4 Prosthesis
5 Guide
6 Releasable fixation with release mechanism
7 TAPAS Graft
8 Anchor
9 Sheath
10 Distal end
11 Proximal end

The invention claimed is:

1. A Trans Aortic Proximal Aortic Stent-Graft [TAPAS-Graft] System for insertion into a blood vessel, comprising a tubular sheath surrounding a folded, self-expanding stent-graft, both internally and externally, such that a sheath outer wall of the sheath lies against the outside of the self-expanding stent-graft and a sheath inner wall lies against the inside of the self-expanding stent-graft and holds the self-expanding stent-graft folded, wherein the self-expanding stent-graft has a proximal end and a distal end, wherein the distal end of the self-expanding stent-graft is surrounded by the sheath in a transition from the sheath inner wall to the sheath outer wall, wherein the self-expanding stent-graft is provided with an anchor at the proximal end, wherein the self-expanding stent-graft is adapted to being deployed from the proximal end to the distal end of the stent-graft by pulling out the sheath, and further comprising a guide in the sheath and releasably connected to the anchor via a release mechanism.

2. A method of using the Trans Aortic Proximal Aortic Stent-Graft [TAPAS-Graft] System according to claim 1, with the steps:

introducing the TAPAS gel via the guide into a blood vessel, releasing the TAPAS graft by fully releasing and deploying the folded, self-expanding stent-graft by pulling out the sheath from the proximal end to the distal end of the stent-graft, and thereby engaging the unsheathed stent-graft on a blood vessel wall;

positioning the unsheathed stent-graft, via the guide releasably connected to the anchor of the unsheathed stent-graft, and releasing the release mechanism releasably connected to the anchor, separating the unsheathed stent-graft from the guide by actuation of the release mechanism, and removing the guide with the sheath.

3. The method according to claim 2, wherein the introducing of the TAPAS-Graft System via the guide into a blood vessel is under image converter (BV) control.

4. A Trans Aortic Proximal Aortic Stent-Graft [TAPAS-Graft] System for insertion into a blood vessel, comprising a tubular sheath surrounding a folded, self-expanding stein-graft both internally and externally, such that a sheath outer wall of the sheath lies against the outside of the self-expanding stent-graft and a sheath inner wall lies against the inside of the self-expanding stent-graft and holds the self-expanding stent-graft folded, wherein the self-expanding stent-graft has a proximal end and a distal end, wherein the distal end of the self-expanding stent-graft is surrounded by the sheath in a transition from the sheath inner wall to the sheath outer wall, wherein the self-expanding stein-graft is provided with an anchor at the proximal end, wherein the self-expanding stent-graft is adapted to be introduced via a guide, the guide located in the sheath, into a blood vessel under image converter (BV) control, wherein the self-expanding stent-graft is adapted to being deployed by pulling out the sheath and guide from the proximal end to the distal end of the self-expanding stent-graft, and wherein the guide is releasably connected to the anchor via a release mechanism, wherein the release mechanism is a cord-splint mechanism.

* * * * *